United States Patent [19]

Rovnyak et al.

[11] Patent Number: 5,103,006

[45] Date of Patent: Apr. 7, 1992

[54] DIHYDROPYRIMIDINE LACTONE DERIVATIVES

[75] Inventors: George C. Rovnyak, Hopewell; Spencer D. Kimball, East Windsor, both of N.J.

[73] Assignee: E. R. Squibb & Sons, Inc., Princeton, N.J.

[21] Appl. No.: 570,664

[22] Filed: Aug. 21, 1990

[51] Int. Cl.⁵ .......................................... C07D 491/048
[52] U.S. Cl. .................... 544/278; 544/584; 544/586; 544/111; 544/296; 540/600
[58] Field of Search ........................................ 544/278

[56] References Cited

U.S. PATENT DOCUMENTS

| | | | |
|---|---|---|---|
| 4,684,656 | 8/1987 | Atwal | 514/274 |
| 4,728,652 | 3/1988 | Atwal | 514/274 |
| 4,855,301 | 8/1989 | Atwal et al. | 514/269 |
| 4,859,676 | 8/1989 | Atwal | 544/278 |

Primary Examiner—Robert T. Bond
Assistant Examiner—Jyothsna Venkat
Attorney, Agent, or Firm—Theodore R. Furman, Jr.; Suzanne E. Babajko

[57] ABSTRACT

Novel compounds of the formula

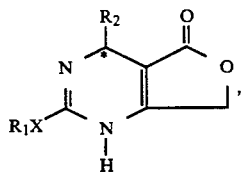

wherein X is sulfur or oxygen, $R_2$ is aryl or heterocyclo and $R_1$ is as defined herein, are disclosed. Compounds of formula I possess calcium channel activating activity.

10 Claims, No Drawings

DIHYDROPYRIMIDINE LACTONE DERIVATIVES

SUMMARY OF THE INVENTION

In accordance with the present invention, novel dihydropyrimidine fused lactone derivatives useful, for example, as cardiovascular agents, are disclosed. The compounds of this invention have the general formula $$\text{I}$$

including pharmaceutically acceptable salts thereof, wherein X is oxygen or sulfur;

$R_1$ is lower alkyl, lower alkenyl, lower alkynyl, $-(CH_2)_m$—cycloalkyl, $(CH_2)_m$—aryl, $-(CH_2)_n$—heterocyclo, $-(CH_2)_p$—OH, $(CH_2)_p$—O—lower alkyl, $-(CH_2)_p$—O—$(CH_2)_m$—aryl, $-(CH_2)_p$—SH, $-(CH_2)_p$—S—lower alkyl, $-(CH_2)_p$—S—$(CH_2)_m$—aryl, $$-(CH_2)_p-N\begin{matrix}R_3\\R_4\end{matrix}, \quad -(CH_2)_n-\overset{O}{\underset{\|}{C}}-N\begin{matrix}R_3\\R_4\end{matrix},$$

$$-(CH_2)_n-\overset{O}{\underset{\|}{C}}-O-R_5, \quad -(CH_2)_p-O-\overset{O}{\underset{\|}{C}}\text{-lower alkyl,}$$

$$-(CH_2)_p-O-\overset{O}{\underset{\|}{C}}-(CH_2)_m\text{-aryl,}$$

or halo substituted lower alkyl;

$R_2$ is aryl or heterocyclo;

$R_3$ and $R_4$ are independently selected from the group consisting of hydrogen, lower alkyl, and $-(CH_2)_m$—aryl or $R_3$ and $R_4$ together with the N atom to which they are attached complete a heterocyclic ring of the formula $R_5$ is hydrogen, lower alkyl, $-(CH_2)_m$—aryl, or a pharmaceutically acceptable salt forming ion;

$R_6$ is hydrogen, lower alkyl of 1 to 4 carbons, lower alkoxy of 1 to 4 carbons, lower alkylthio of 1 to 4 carbons, halo, hydroxy, or $CF_3$;

$R_7$ is hydrogen, lower alkyl of 1 to 4 carbons, m is zero or an integer from 1 to 6;
n is an integer from 1 to 6; and,
p is integer from 2 to 6.

DETAILED DESCRIPTION OF THE INVENTION

This invention in its broadest aspects relates to the dihydropyrimidine compounds of formula I above, to compositions and the method of using such compounds as cardiovascular agents.

The term lower alkyl used in defining various symbols refers to straight or branched chain saturated hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated carbocyclic rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, monosubstituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —N-H—alkyl wherein alkyl is of 1 to 4 carbons, —N(alkyl)$_2$ wherein alkyl is of 1 to 4 carbons, $CF_3$, NCS, OCHF$_2$, -continued

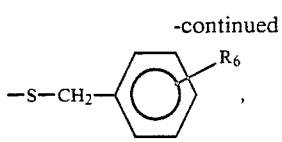

—O—CH$_2$—cycloalkyl, or —S—CH$_2$—cycloalkyl, and disubstituted phenyl, 1-naphthyl, or 2-naphthyl wherein said substituents are selected from methyl, methoxy, methylthio, halo, CF$_3$, nitro, amino, and OCHF$_2$.

The term heterocyclo refers to fully saturated or unsaturated rings of 5 or 6 atoms containing one to four N atoms, or one O atom, or one S atom, or one O atom and one or two N atoms, or one S atom and one or two N atoms. The heterocyclo ring is attached by way of an available carbon atom. Preferred monocyclic heterocyclo groups include 2- and 3-thienyl, 2- and 3-furyl, 2-, 3- and 4-pyridyl, and imidazolyl. The 2-, 3- and 4-pyridyl may also have a substituent selected from lower alkyl of 1 to 4 carbons, lower alkoxy of 1 to 4 carbons, and lower alkylthio of 1 to 4 carbons on an available carbon. The preferred substituted pyridyl is 2-methylthio-3-pyridinyl. The term heterocyclo also includes bicyclic rings wherein the five or six membered ring containing O, S and N atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

To prepare the compounds of the present invention, a compound of the formula

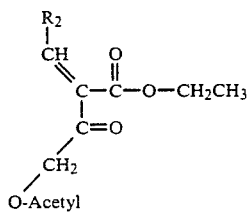

II can be reacted in a solvent, such as dimethylformamide, with a compound of the formula

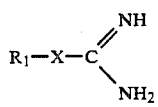

III to provide a compound of the formula

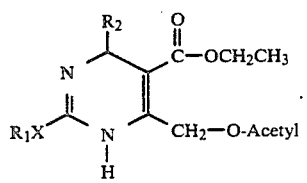

IV

Intermediate IV, in solvents, e.g., methanol and dimethylsulfoxide, can thereafter be treated with a base, such as sodium hydroxide, to provide compounds of formula I.

Intermediates of formula II can be prepared by reacting an aldehyde of the formula $$R_2—CHO \qquad (V)$$

with an ester of the formula

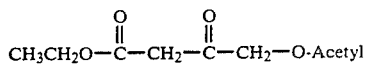

VI in an aprotic, nonpolar solvent, e.g., benzene containing a catalytic amount of piperidine and acetic acid.

If any of R$_1$ and R$_2$ in the above reactions are aryl or —(CH$_2$)$_m$—aryl wherein aryl is phenyl substituted with one hydroxy or one or more amino groups, heterocyclo or —(CH$_2$)$_n$—heterocyclo wherein the heterocyclo ring contains an NH such as imidazolyl, or a substituted alkyl such as —(CH$_2$)$_n$—OH, —(CH$_2$)$_p$—OH, —(CH$_2$)$_p$—NH$_2$, —(CH$_2$)$_n$—SH, —(CH$_2$)$_p$—SH, or

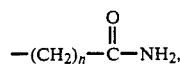

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

R$_1$ is lower alkyl of 1 to 5 carbons, especially methyl or pentyl, lower alkenyl of 3 to carbons, especially 2-propenyl, benzyl, 4-methoxybenzyl, or

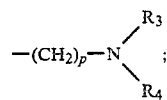

p is 2, 3 or 4;

R$_3$ and R$_4$ are independently selected from hydrogen, lower alkyl of 1 to 5 carbons, and benzyl;

R$_2$ is phenyl, mono substituted phenyl wherein said substituent is at the 2- or 3-position and is lower alkyl of 1 to 4 carbons, lower alkoxy of 1 to 4 carbons, lower alkylthio of to 4 carbons, halo, CF$_3$, nitro, or OCHF$_2$, or disubstituted phenyl at the 2- and 3-positions wherein said substituents are selected from methyl, methoxy, methylthio, halo, CF$_3$, nitro, or OCHF$_2$.

Most preferred are the above compounds wherein X is sulfur;

R$_1$ is methyl; and

R$_2$ is 3-nitrophenyl, 2-(methylthio)phenyl, 2-(butylthio)phenyl, 2-(butylthio)-3-nitrophenyl, or 2-(butylthio)-5-nitrophenyl.

The compounds of formula I have been represented structurally as 1,4-dihydropyrimidines. However, such structures are tautomeric and can also be structurally represented as 3,4-dihydropyrimidines, i.e.,

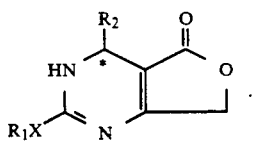

Both forms are within the scope of this invention.

The compounds of formula I contain an asymmetric center within the dihydropyrimidine ring as represented by the *. Thus, the compounds of formula I can exist in enantiomeric forms or in mixtures thereof. When enantiomeric products are prepared, they can be separated by chromatography on a chiral HPLC column (e.g., chiralcel OD, Diacel, Inc.).

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_1$ is

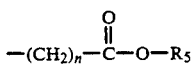

include carboxylic acid salts, i.e., $R_5$ is a pharmaceutically acceptable salt forming ion. Preferred salt forming ions include alkali metal salt ions such as sodium, potassium, and lithium, and alkaline earth metal salt ions such as calcium and magnesium.

The compounds of formula I and the pharmaceutically acceptable salts thereof are useful as cardiovascular agents. These compounds act as calcium channel activators and are positive inotropic agents which are useful, for example, for treatment of heart failure, and may also be useful for hypotension, shock and endocrinological disorders. The compounds are given in a single dose, or preferably two to four divided daily doses, on a basis of about 0.1 to 100 mg per kilogram of body weight per day, preferably from about 1 to about 50 mg per kilogram per day. The substance is preferably administered orally, but parenteral routes such as the subcutaneous, intramuscular, or intravenous routes can also be employed.

The compounds of formula I can be formulated for use in compositions such as tablets, capsules or elixirs for oral administration, or in sterile solutions or suspension for parenteral administration. About 10 to 500 mg of a compound of formula I is compounded with physiologically acceptable vehicle, carrier, excipient, binder, preservative stabilizer, flavor, etc., in a unit dosage form as called for by accepted pharmaceutical practice. The amount of active substance in these compositions or preparations is such that a suitable dosage in the range indicated is obtained.

The following examples are illustrative of the invention.

EXAMPLE 1

4,7-Dihydro-2-(methylthio)-4-[2-(methylthio)-3-nitrophenyl]furo[3,4-d]pyrimidin -5-(1H)-one, monohydrochloride A. 4-(Acetyloxy)-2-[[2-(methylthio)-3-nitrophenyl]-methylene]-3-oxobutanoic acid, ethyl ester A mixture of 1.60 g (0.0081 mole) of 3-nitrobenzaldehyde, 1.90 g (0.0100 mole) of ethyl-4-acetoxyacetoacetate (Tet. 28, 967 (1972)), 0.2 ml of piperidine, 0.2 ml of HOAc and 10 g (0.0830 mole) of magnesium sulfate in 75 ml of benzene was stirred overnight at room temperature, then diluted with ethyl acetate and extracted with 1N hydrochloric acid, saturated sodium hydrogen carbonate and brine. The dried solution was concentrated in vacuo to give 3.53 g of crude product, which was combined with another 1.92 g of the material prepared in an earlier experiment.

Flash chromatography using ethyl acetate/hexane 1:3 gave 3.79 g of the title A compound as an oil.

B. 1,4-Dihydro-6-(hydroxymethyl)-2-(methylthio)-4-[2-(methylthio)-3-nitrophenyl]-5-pyrimidinecarboxylic acid, ethyl ester A stirred mixture of 1.77 g (0.0048 mole) of the title A compound, 0.65 g (0.0024 mole) of 2-methyl-2-thiopseudourea sulfate and 0.39 g (0.0048 mole) of sodium acetate in 12 ml of dimethylformamide was heated at 65° for 6 hours.

The mixture was diluted with ethyl acetate and washed twice with water and brine, then dried and concentrated in vacuo to give 1.8 g of crude product. Flash chromatography using ethyl acetate/hexane 1:2 gave 0.54 g of the title B compound as an oil. This was combined with 0.17 g of similar material (total 0.71 g, 0.0017 mole).

C. 4,7-Dihydro-2-(methylthio)-4-[2-(methylthio)-3-nitrophenyl]furo[3,4-d]pyrimidin-5(1H)-one, monohydrochloride A solution of the title B compound (0.71 g, 0.0017 mole) in 12 ml of methanol, 2 ml of dimethylsulfoxide and 1.78 ml of 1N sodium hydroxide (0.0017 mole) was stirred at room temperature for 1.5 hours, then diluted with ethyl acetate and washed with water (2x) and brine. The dried solution was concentrated to approximately 20 ml and cooled overnight to give 0.39 g of cream colored product, m.p. 235°-236°. The above was dissolved in 4 ml of 50% $CHCl_3$/MeOH and treated with 1 eq. of ethereal hydrochloric acid to crystallize 0.33 g of the title compound, m.p. 198°-200°.

Analysis calc'd for $C_{14}H_{13}N_3O_4S_2 \cdot HCl$:
C, 42.37; H, 3.81; N, 10.59; Cl, 8.93; S, 16.16;
Found: C, 42.27; H, 3.59; N, 10.43; Cl, 9.20; S, 16.40.

EXAMPLE 2

4,7-Dihydro-2-(methylthio)-4-[2-(methylthio)-5-nitrophenyl]furo[3,4-d]pyrimidin -5(1H)-one, monohydrochloride A. 4-(Acetyloxy)-2-[[2-(methylthio)-5-nitrophenyl]-methylene]-3-oxobutanoic acid, ethyl ester A solution of 2-methylthio, 5-nitrobenzaldehyde (1.60 g, 8.12 mmole) and ethyl-4-acetoxyacetoacetate (1.90 g, 10.15 mmole, Tet., 28, 967 (1972)) in 75 ml of benzene containing 10 g of anhydrous magnesium sulfate was treated with piperidine (0.2 ml) and acetic acid (0.2 ml). After stirring overnight at room temperature (reaction is incomplete but by-product formation becomes unacceptable with extended reaction times), the mixture was diluted with ethyl acetate and washed with 1N hydrochloric acid, water, saturated sodium hydrogen carbonate, water and brine. The dried (MgSO$_4$) organic solution was concentrated in vacuo and the residue (ca 3.5 g) flash chromatographed on 400 ml of LPS-1 SiO$_2$, eluting with ethyl acetate/hexane (2:5) to give 0.78 g of the title A compound as an oil.

B. 1,4-Dihydro-6-(hydroxymethyl)-2-(methylthio)-4-[2-(methylthio)-5-nitrophenyl]-5-pyrimidinecarboxylic acid, ethyl ester A solution of the title A compound (1.06 g, 2.88 mmol) in 10 ml of dimethylformamide under argon at room temperature was treated with 2-methyl-2-thiopseudourea sulfate (0.42 g, 1.51 mmol) and sodium acetate (0.24 g, 3.02 mmol), then heated at 70° for 6 hours. The dark mixture was diluted with ethyl acetate and washed with saturated sodium hydrogen carbonate, water and brine. The dried (MgSO$_4$) organic fraction was concentrated in vacuo to give 1.2 g of a dark oil. Flash chromatography and elution with ethyl acetate/hexane (2:3) gave 0.36 g of the title B compound as an oil.

C. 4,7-Dihydro-2-(methylthio)-4-[2-(methylthio)-5-nitrophenyl]furo[3,4-d]pyrimidin-5(1H)-one A solution of the title B compound (0.36 g, 0.90 mmol) in 10 ml of ethanol at room temperature was treated with 1 ml of 1N sodium hydroxide. After stirring for 0.5 hours, the mixture was diluted with ethyl acetate and washed with water and brine. The dried (MgSO$_4$) organic fraction was concentrated in vacuo to give 0.34 g. Trituration with hot ethyl acetate, cooling and filtration gave 0.18 g of the title C compound, m.p. 56°–257.5°.

D. 4,7-Dihydro-2-(methylthio)-4-[2-(methylthio)-5-nitrophenyl]furo[3,4-d]pyrimidin-5(1H)-one, monohydrochloride A solution of the title C compound (0.31 g, 0.88 mmol) in warm MeOH/CHCl$_3$ (1:1) was treated with excess ethereal hydrochloric acid. Volatiles were reduced in vacuo and the product salt slowly crystallized to give 0.33 g of the title compound, m.p. 285° d (required drying at 100° in vacuo to remove CHCl$_3$ solvent).

Analysis calc'd for C$_{14}$H$_{13}$N$_3$O$_4$S$_2$·HCl:
C, 43.35; H, 3.64; N, 10.83; Cl, 9.14;
S, 16.53;
Found: C, 43.42; H, 3.44; N, 10.78; Cl, 9.11;
S, 16.21.

EXAMPLE 3

4,7-Dihydro-2-(methylthio)-4-(3-nitrophenyl)furo[3,4-d]pyrimidin-5(1H)-one

A. 4-(Acetyloxy)-2-[(3-nitrophenyl)methylene]-3-oxobutanoic acid, ethyl ester

A solution of ethyl 4-acetoxyacetoacetate (23.0 g, 0.122 mole, Tet., 28, 967 (1972)) and 3-nitrobenzaldehyde (18.47 g, 0.122 mole) in 125 ml of benzene was treated with HOAc (0.6 ml) and piperidine (0.6 ml) and heated at reflux temperature. Collection of water ceased after 0.5 hour; therefore, additional HOAc (1 ml) and piperidine (1 ml) were added and refluxing continued. A total of 2.0 ml water was collected. The cooled mixture was washed with water (2x) and saturated brine, dried over anhydrous magnesium sulfate, treated with Darco to remove color and concentrated in vacuo to give an oil that solidified on standing. Trituration with IPE/Et$_2$O/Hexane and stirring overnight to pulverize the solids afforded 24.2 g of the title A compound, m.p. 88°–95°.

Analysis calc'd for C$_{15}$H$_{15}$NO$_7$:
C, 56.07; H, 4.71; N, 4.36;
Found: C, 55.83; H, 4.68; N, 4.20.

B. 1,4-Dihydro-6-(hydroxymethyl)-2-(methylthio)-4-(3-nitrophenyl)-5-pyrimidinecarboxylic acid, ethyl ester The title A compound (5.0 g, 0.0156 mole) and 2-methyl-2-thiopseudourea sulfate (2.17 g, 0.0078 mole) in 25 ml of dimethylformamide under argon was treated with sodium acetate (1.28 g, 0.0156 mole) and heated at 85°–90° for 2 hours. The cooled reaction mixture was diluted with ethyl acetate and washed with water (2x) and saturated brine. The organic fraction was dried over anhydrous magnesium sulfate and concentrated in vacuo to give 6 g of a dark oil (resistant to purification via oxalate salt). Flash chromatography and elution with ethyl acetate/hexane (2:3) gave a total of 1.6 g of the title B compound.

Analysis calc'd for C$_{17}$H$_{19}$N$_3$O$_6$S:
C, 51.90; H, 4.87; N, 10.68; S, 8.15;
Found: C, 51.93; H, 5.02; N, 10.05; S, 7.34.

C. 4,7-Dihydro-2-(methylthio)-4-(3-nitrophenyl)furo[3,4-d]pyrimidin-5(1H)-one

The title B compound (1.6 g, 4.07 mmole) in 20 ml of ethanol at room temperature was treated with 5 ml of 1N sodium hydroxide. After 0.5 hour, the mixture was partitioned between ethyl acetate and water. The organic fraction was washed with saturated brine, dried over anhydrous magnesium sulfate and concentrated in vacuo to give 1.34 g of a residue that solidified. Trituration with hot ethyl acetate/acetone and cooling gave 0.66 g of the title compound, m.p. 204°–206°.

Analysis calc'd for C$_{13}$H$_{11}$N$_3$O$_4$S:
C, 51.14; H, 3.63; N, 13.76; S, 10.50;
Found: C, 51.31; H, 3.75; N, 13.79; S, 10.49.

EXAMPLE 4

4-[2-(Butylthio)phenyl]-4,7-dihydro-2-(methylthio)furo[3,4-d]pyrimidin-5(1H)-one, monohydrochloride A. 2-(Butylthio)benzoic acid A stirred solution of n-bromobutane (12.4 g, 0.09 mole) in 90 mL of ethanol under argon at room temperature was treated with a solution of thiosalicylic acid (13.5 g, 0.09 mole) in 72 mL of 10% sodium hydroxide. After stirring overnight, volatiles were stripped in vacuo and the residue was diluted with water and acidified with concentrated hydrochloric acid to precipitate the product. The crude product was collected and air dried, then dissolved in hot acetonitrile containing 1–2 mL of water. Upon cooling there was obtained 13.7 g of the title A compound, m.p. 96°–101°.

B. 2-(Butylthio)benzenemethanol

A stirred slurry of lithium aluminum hydride (2.92 g, 0.077 mole) in 100 mL of tetrahydrofuran under argon at 0°–5° was treated dropwise with a solution of the title A compound (16.16 g, 0.077 mole) in 50 mL of tetrahydrofuran. After completing the addition, the mixture was allowed to warm to room temperature then was heated at 70° for 15 minutes. The mixture, cooled to 10°, was carefully treated with 2.95 mL of water, 2.95 mL of 15% sodium hydroxide and 2.95 mL of water. The granular precipitate was removed by filtration and the filtrate concentrated in vacuo. The residue, dissolved in ethyl acetate, was washed with saturated sodium hydrogen carbonate, water and brine. The organic solution (dried over anhydrous magnesium sulfate) was concentrated in vacuo to give 14.21 g of an oil. Distillation provided 13.68 g of the title B compound, b.p. 107°/0.4 mm Hg.

C. 2-(Butylthio)benzaldehyde

The method of Swern (Tet., 34, 1651 (1978)) was used to oxidize the title B alcohol to the title C aldehyde. Thus, from the title B compound (13.6 g, 0.069 mole) there was obtained 12.43 g of the title C compound, b.p. 100°-101°/0.4 mm Hg.

D. 4-(Acetoxy)-2-[[2-(butylthio)phenyl]methylene]-3-oxobutanoic acid, ethyl ester A solution of the title C compound (6.0 g, 0.030 mole) and ethyl 4-acetoxyacetoacetate (3.56 g, 0.03 mole, Tet., 28, 967 (1972)) in 50 mL of benzene was treated with piperidine (0.6 mL) and HOAc (0.3 mL) and heated at reflux temperature, collecting formed water of reaction. After 1 hour, the mixture was diluted with ethyl acetate and washed with water (2x) and brine. The dried (anhydrous magnesium sulfate) solution was concentrated to give 8 g of an oil. Flash chromatography and elution with ethyl acetate/hexane (1:6) gave 2.25 g of unreacted title C aldehyde and 4.13 g of the title D compound.

E. 4-[2-(Butylthio)phenyl-1,4-dihydro-6-(hydroxymethyl)-2-(methylthio)-5-pyrimidinecarboxylic acid, ethyl ester A solution of the title D compound (2.0 g, 5.48 mmole) and 2-methyl 2-thiopseudourea sulfate (0.76 g, 2.74 mmole) in 10 ml of dimethylformamide under argon at room temperature was treated with sodium acetate (0.46 g, 5.48 mmole), then heated at 70° for 6 hours. The reaction mixture, diluted with ethyl acetate, was washed with saturated sodium hydrogen carbonate, water and brine. The dried (anhydrous magnesium sulfate) organic solution was concentrated in vacuo to give 2.4 g of an oil. Flash chromatography and elution with ethyl acetate/hexane (1:3) gave 0.71 g of the title E compound.

F. 4-[2-(Butylthio)phenyl]-4,7-dihydro-2-(methylthio)furo[3,4-d]pyrimidin-5(1H)-one, monohydrochloride A solution of the title E compound (0.60 g, 1.52 mmole) in 10 mL of ethanol was treated with 1.5 mL of 1N sodium hydroxide. After 0.5 hour, volatiles were removed in vacuo and the residue, dissolved in ethyl acetate, was washed with water (2x) and brine. The dried (anhydrous magnesium sulfate) organic solution was concentrated to give 0.51 g of crude product, m.p. 45°-60°. This was taken up in acetonitrile and treated with excess ethereal hydrochloric acid. Volatiles were stripped to a foam which was triturated with ether to give 0.51 g of the title compound.

Analysis calc'd for $C_{17}H_{20}N_2O_2S_2 \cdot HCl$:
C, 53.04; H, 5.50; N, 7.28; S, 16.66; Cl, 9.21;
Found: C, 53.06; H, 5.37; N, 7.50; S, 16.41; Cl, 9.40.

EXAMPLE 5

4,7-Dihydro-2-(methylthio)-4-[2-(methylthio)phenyl-furo[3,4-d]pyrimidin-5(1H)-one, monohydrochloride A. 4-(Acetyloxy)-2-[[2-methylthio)phenyl]methylene]-3-oxobutanoic acid, ethyl ester A solution of 10.0 g (0.065 mole) of 2-(methylthio)benzaldehyde [J. Org. Chem., Vol. 37, p. 3824, 1972 (Swern oxidation)], 12.3 g (0.065 mole) of ethyl 4-acetoxyacetoacetate, 1.5 ml of piperidine and 1.5 ml of HOAc in 250 ml of benzene was refluxed for 2 hours, collecting one equivalent of water. The solvent was evaporated and the residue, in ethyl acetate, was washed with potassium hydrogen sulfate, sodium hydrogen carbonate, water and brine. The dried solution was evaporated to yield 19.5 g of the title A compound as an oil.

B. 1,4-Dihydro-6-(hydroxymethyl)-2-(methylthio)-4-[2-(methylthio)phenyl]-5-pyrimidinecarboxylic acid, ethyl ester A mixture of 5.0 g (0.0155 mole) of the title A compound, 2.15 g (0.0077 mole) of 2-methyl-2-thiopseudourea sulfate and 1.27 g (0.0155 mole) of sodium acetate in 40 ml of dimethylformamide was stirred for 6 hours at 70°, diluted with ethyl acetate and washed with water (2x) and brine. The solution was dried and evaporated to give 4.3 g of crude product (oil). Flash chromatography using ethyl acetate/hexane 1:3 afforded 1.7 g of the title B compound as a yellow solid, m.p. 151°-153°.

C. 4,7-Dihydro-2-(methylthio)-4-[2-(methylthio)phenyl]furo[3,4-d]pyrimidin-5(1H)-one, monohydrochloride A solution of 1.6 g (0.004 mole) of the title B compound, 4.4 ml 1N sodium hydroxide (0.0044 mole) in 30 ml of ethanol was stirred for 30 minutes. Approximately one half of the alcohol was evaporated at 30°. The solution was diluted with ethyl acetate and extracted with water (2x) and brine, then dried and evaporated in vacuo to give 1.1 g of a yellow solid, m.p. 164°-166°.

The above was dissolved in 20 ml of warm acetonitrile, cooled and treated with one equivalent of ethereal hydrochloric acid to yield 1.0 g of solid. This material was triturated with 10 ml of warm ethanol to give 0.96 g of the title compound as a cream-colored product, m.p. 219°-221° dec.

Analysis calc'd for $C_{14}H_{14}N_2O_2S_2 \cdot HCl$:
C, 49.04; H, 4.41; N, 8.17; Cl, 10.34; S, 18.70;
Found: C, 49.04; H, 4.44; N, 8.12; Cl, 10.63; S, 18.53.

EXAMPLES 6-13

Using the methodology described above, the following additional compounds are prepared.

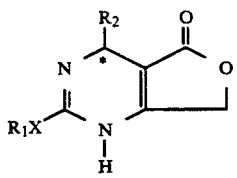

| Ex. | $R_1$ | $R_2$ | X |
|---|---|---|---|
| 6 | $CH_2CH_3$ | 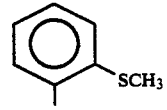 | S |
| 7 | $CH_2-$⌬ | 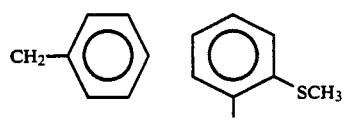 | S |

-continued

| Ex. | R₁ | R₂ | X |
|---|---|---|---|
| 8 | CH₃CH₂N(CH₃)CH₃ | 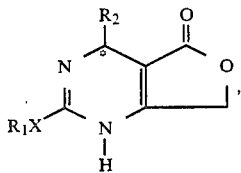 (phenyl-SCH₃) | S |
| 9 | CH₃ | (phenyl-Cl) | S |
| 10 | CH₃ | (phenyl-CF₃) | S |
| 11 | CH₃ | (phenyl-NO₂) | S |
| 12 | CH₃ | (pyridyl-N) | S |
| 13 | CH₂-phenyl | furanyl-O | S |

What is claimed is:

1. A compound of the formula

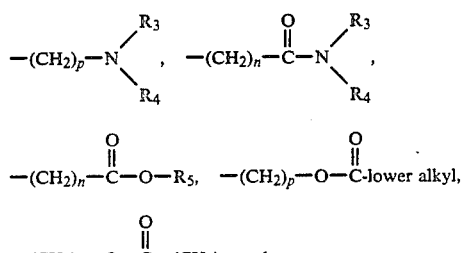

including pharmaceutically acceptable salts thereof, wherein X is oxygen or sulfur;

R₁ is lower alkyl, lower alkenyl, lower alkynyl, —(CH₂)$_m$—cycloalkyl, —(CH₂)$_m$—aryl, —(CH₂)$_n$—OH, —(CH₂)$_p$—O—lower alkyl, —(CH₂)$_p$—O—(CH₂)$_m$—aryl, —(CH₂)$_n$—SH, —(CH₂)$_p$—S—lower alkyl, —(CH₂)$_p$—S—(CH₂)$_m$—aryl, —(CH₂)$_p$—N(R₃)(R₄),  —(CH₂)$_n$—C(O)—N(R₃)(R₄), —(CH₂)$_n$—C(O)—O—R₅,  —(CH₂)$_p$—O—C(O)—lower alkyl, —(CH₂)$_p$—O—C(O)—(CH₂)$_m$-aryl, or halo substituted lower alkyl;

R₂ is aryl; and

R₃ and R₄ are independently selected from the group consisting of hydrogen, lower alkyl, and —(CH₂)$_m$—aryl;

R₅ is hydrogen, lower alkyl, —(CH₂)$_m$—aryl, or a pharmaceutically acceptable salt forming ion;

R₆ is hydrogen, lower alkyl of 1 to 4 carbons, lower alkoxy of 1 to 4 carbons, lower alkylthio of 1 to 4 carbons, halo, hydroxy, or CF₃;

m is zero or an integer from 1 to 6;

n is an integer from 1 to 6; and p is an integer from 2 to 6;

wherein if not otherwise defined above, the term "lower alkyl" denotes straight or branched chain saturated hydrocarbon radicals having up to eight carbons;

the term "lower alkenyl" denotes straight or branched chain hydrocarbon radicals having from two to eight carbons and one double bond;

the term "lower alkynyl" denotes straight or branched chain hydrocarbon radicals having from two to eight carbons and one triple bond;

the term "cycloalkyl" denotes saturated carbocyclic rings of four to seven carbon atoms;

the term "aryl" denotes phenyl, 1-naphthyl, or 2-naphthyl, or monosubstituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —NH—alkyl wherein alkyl is of 1 to 4 carbons, —N(alkyl)₂ wherein alkyl is of 1 to 4 carbons, NCS, OCHF₂,

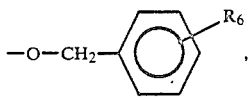

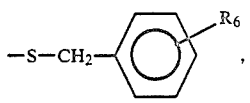

—O—CH₂—cycloalkyl, or —S—CH₂—cycloalkyl, or denotes disubstituted phenyl, 1-naphthyl, or 2-naphthyl wherein said substituents are selected from methyl, methoxy, lower alkylthio of 1 to 4 carbons, halo, CF₃, nitro, amino, and OCHF₂.

2. A compound in accordance with claim 1 wherein R₁ is lower alkyl of 1 to 5 carbons, lower alkenyl of 3 to 5 carbons, benzyl, 4-methoxybenzyl, or

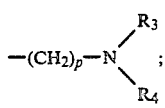

p is 2, 3 or 4;

R₃ and R₄ are independently selected from hydrogen, lower alkyl of 1 to 5 carbons, and benzyl;

R₂ is phenyl, mono substituted phenyl wherein said substituent is at the 2- or 3-position and is lower alkyl of 1 to 4 carbons, lower alkoxy of 1 to 4 carbons, lower alkylthio of 1 to 4 carbons, halo, CF₃, nitro, or OCHF₂, or disubstituted phenyl at the 2- and 3-positions wherein said substituents are selected from methyl, methoxy, methylthio, halo, CF$_3$, nitro, or OCHF$_2$.

3. A compound in accordance with claim 1 wherein
X is sulfur;
R$_1$ is methyl; and
R$_2$ is 3-nitrophenyl, 2-(methylthio)phenyl, 2-(butylthio)phenyl, 2-(methylthio)-3-nitrophenyl, or 2-(methylthio)-5-nitrophenyl.

4. A compound in accordance with claim 1 having the name 4,7-dihydro-2-(methylthio)-4-[2-(methylthio)-3-nitrophenyl]furo[3,4-d]pyrimidin -5(1H)-one, monohydrochloride.

5. A compound in accordance with claim 1 having the name 4,7-dihydro-2-(methylthio)-4-[2-(methylthio)-5-nitrophenyl]furo[3,4-d]pyrimidin -5(1H)-one, monohydrochloride.

6. A compound in accordance with claim 1 having the name 4,7-dihydro-2-(methylthio)-4-(3nitrophenyl)-furo[3,4-d]pyrimidin-5(1H)-one.

7. A compound in accordance with claim 1 having the name 4-[2-(butylthio)phenyl-4,7-dihydro-2-(methylthio)furo[3,4-d]pyrimidin -5(1H)one, monohydrochloride.

8. A compound in accordance with claim 1 having the name 4,7-dihydro-2-(methylthio)-4-[2(methylthio)-phenyl]furo[3,4-dpyrimidin-5(1H)-one, monohydrochloride.

9. A compound in accordance with claim 2 wherein R$_1$ is methyl, pentyl, or 2-propenyl.

10. A compound of claim 1, wherein said term "aryl" is defined as denoting phenyl, 1-naphthyl, or 2-naphthyl, or monosubstituted phenyl, 1-naphthyl, or 2-naphthyl wherein said substituent is lower alkyl of 1 to 4 carbons, lower alkythio of 1 to 4 carbons, lower alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, CF$_3$, NCS, OCHF$_2$,

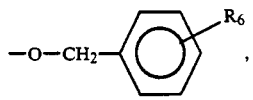

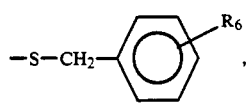

—O—CH$_2$—cycloalkyl, or —S—CH$_2$—cycloalkyl, or denoting disubstituted phenyl 1-naphthyl, or 2-naphthyl wherein (a) for phenyl, 1-naphthyl or 2-naphthyl said two substituents are selected from methyl, methoxy, methylthio, halo, CF$_3$, nitro, amino, and OCHF$_2$, or (b) for disubstituted phenyl, said two substituents are butylthio and nitro.

* * * * *